(12) United States Patent
Neumann

(10) Patent No.: US 11,955,224 B2
(45) Date of Patent: Apr. 9, 2024

(54) SYSTEM AND METHOD FOR GENERATING A PULMONARY DYSFUNCTION FUNCTIONAL PROGRAM

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 183 days.

(21) Appl. No.: 17/387,325

(22) Filed: Jul. 28, 2021

(65) Prior Publication Data

US 2022/0208346 A1   Jun. 30, 2022

Related U.S. Application Data

(63) Continuation-in-part of application No. 17/136,087, filed on Dec. 29, 2020, now Pat. No. 11,145,400.

(51) Int. Cl.
*G16H 20/60* (2018.01)
*G16H 10/60* (2018.01)
*G16H 50/20* (2018.01)

(52) U.S. Cl.
CPC .............. *G16H 20/60* (2018.01); *G16H 10/60* (2018.01); *G16H 50/20* (2018.01)

(58) Field of Classification Search
CPC ..... G16H 50/20; A61B 5/02055; G16B 40/20
See application file for complete search history.

(56) References Cited

U.S. PATENT DOCUMENTS

| 5,179,080 | A | 1/1993 | Rothkopf |
| 10,271,791 | B2 | 4/2019 | Donnelly |
| 10,565,897 | B2 | 2/2020 | Crepp |
| 10,762,990 | B1 | 9/2020 | Schilling |
| 10,846,622 | B2 | 11/2020 | Neumann |
| 2006/0031102 | A1* | 2/2006 | Teller ..................... A61B 5/411 600/300 |

(Continued)

OTHER PUBLICATIONS https://link.springer.com/article/10.1007/s11517-018-1798-z; Title: Continuous remote monitoring of COPD patients—justification and explanation of the requirements and a survey of the available technologies; By: Ivan Tomasic; Date: 2018.

(Continued)

*Primary Examiner* — Fabricio R Murillo Garcia
(74) *Attorney, Agent, or Firm* — Caldwell Intellectual Property Law

(57) ABSTRACT

A system for generating a pulmonary dysfunction nourishment program includes a computing device configured to receive at least a respiratory volume collection relating to a user, produce at least a respiratory parameter of a plurality of respiratory parameters as a function of the at least a respiratory volume collection, identify a functional signature as a function of the at least a respiratory parameter, wherein identifying further comprises receiving a conduct indicator, and identifying the functional signature as a function of the conduct indicator, the at least a respiratory parameter, and a functional machine-learning model, and generate a functional program as a function of the functional signature.

20 Claims, 9 Drawing Sheets

(56) References Cited

U.S. PATENT DOCUMENTS

| | | | | |
|---|---|---|---|---|
| 2020/0043592 A1* | 2/2020 | Mehta | ............... | A61M 60/295 |
| 2020/0163843 A1* | 5/2020 | Francis | ............... | G16H 10/60 |
| 2020/0380421 A1* | 12/2020 | Neumann | ............ | G06V 10/774 |
| 2020/0380458 A1 | 12/2020 | Neumann | | |
| 2021/0020294 A1* | 1/2021 | Bharmi | ............... | G16H 50/30 |
| 2022/0280040 A1* | 9/2022 | Javed | ............... | A61B 5/7275 |

OTHER PUBLICATIONS https://www.mdpi.com/2072-6643/11/6/1357/htm; Title: Role of Diet in Chronic Obstructive Pulmonary Disease Prevention and Treatment; By: Egeria Scoditti; Date: 2019.

\* cited by examiner

SYSTEM AND METHOD FOR GENERATING A PULMONARY DYSFUNCTION FUNCTIONAL PROGRAM

CROSS-REFERENCE TO RELATED APPLICATIONS

This application is a continuation-in-part of Non-provisional application Ser. No. 17/136,087 filed on Dec. 29, 2020 and entitled "SYSTEM AND METHOD FOR GENERATING A PULMONARY DYSFUNCTION NOURISHMENT PROGRAM," the entirety of which is incorporated herein by reference.

FIELD OF THE INVENTION

The present invention generally relates to the field of artificial intelligence. In particular, the present invention is directed to a system and method for generating a pulmonary dysfunction nourishment program.

BACKGROUND

Current edible suggestion systems do not account for pulmonary characteristics of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating a pulmonary dysfunction nourishment program includes a computing device configured to receive at least a respiratory volume collection relating to a user, produce at least a respiratory parameter of a plurality of respiratory parameters as a function of the at least a respiratory volume collection, identify a functional signature as a function of the at least a respiratory parameter, wherein identifying further comprises receiving a conduct indicator, and identifying the functional signature as a function of the conduct indicator, the at least a respiratory parameter, and a functional machine-learning model, and generate a functional program as a function of the functional signature.

In another aspect a method for generating a pulmonary dysfunction functional program includes receiving, by a computing device, at least a respiratory volume collection relating to a user, producing, by the computing device, at least a respiratory parameter of a plurality of respiratory parameters as a function of the respiratory volume collection, identifying, by the computing device, a functional signature as a function of the at least a respiratory parameter, wherein identifying comprises receiving a conduct indicator, and identifying the functional signature as a function of the conduct indicator, the at least a respiratory parameter, and a functional machine-learning model, and generating, by the computing device, a functional program as a function of the functional signature.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a pulmonary dysfunction functional program. In an embodiment, the disclosure may receive at least a respiratory volume relating to a user. Aspects of the present disclosure can be used to produce at least a respiratory parameter as a function of the respiratory volume collection using respiratory algorithms. Aspects of the present disclosure can be used to identify a functional signature as a function of the pulmonary bundle element. This is so, at least in part, because disclosure utilizes a functional machine-learning model. Aspects of the present disclosure allow for generating a functional program. Exemplary embodiments illustrating aspects of the present disclosure are described below in the context of several specific examples.

Figure 1:
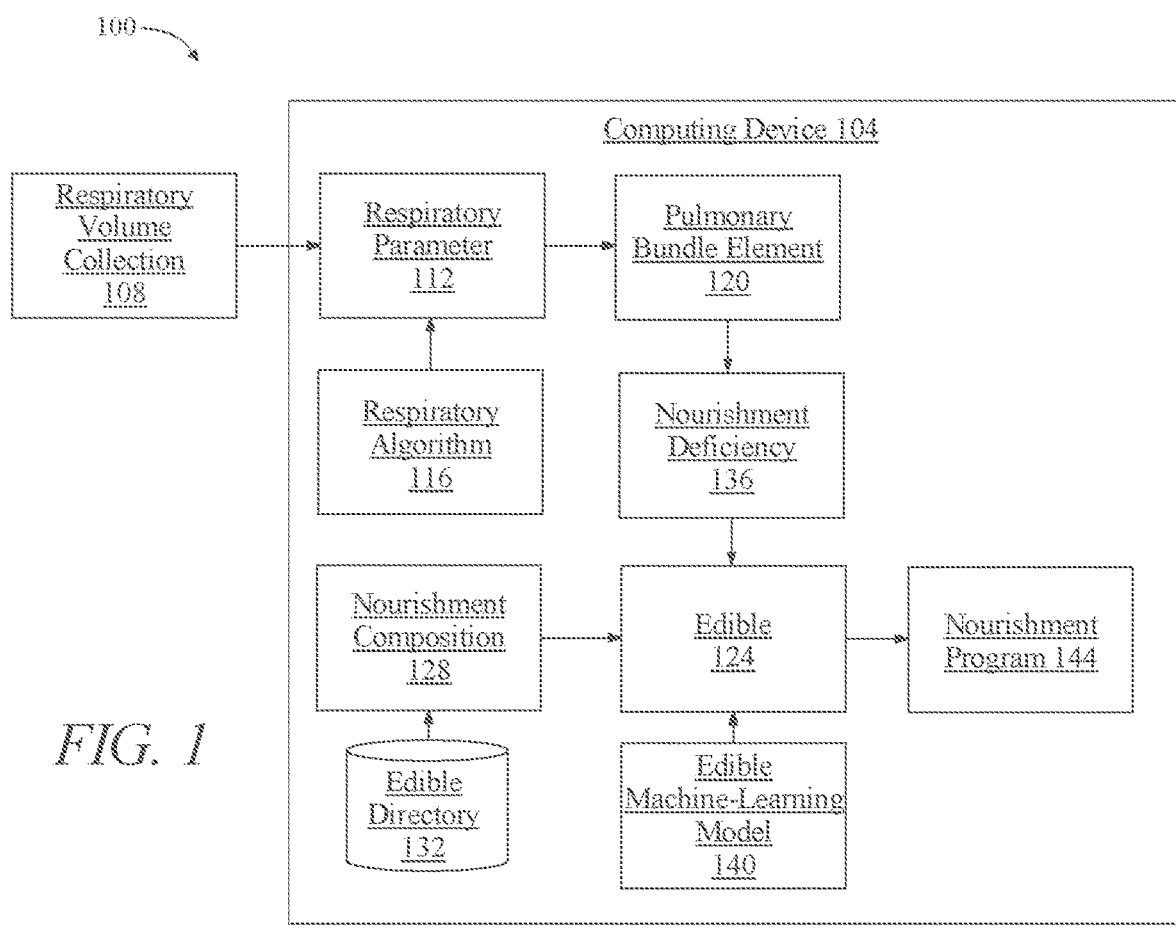
FIG. 1 is a block diagram illustrating an exemplary embodiment of a system for generating a pulmonary dysfunction nourishment program.

Referring now to FIG. 1, an exemplary embodiment of a system 100 for generating a pulmonary dysfunction nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 receives at least a respiratory volume collection 108 relating to a user. As used in this disclosure "respiratory volume collection" is a volume of biological sample from an individual associated with the respiratory system of an individual. A biological sample may include, without limitation, exhalate, blood, sputum, urine, saliva, feces, semen and other bodily fluids, as well as tissue. Exhalate may include, without limitation, breath that is expelled from an individual via breathing and/or some other forced exhalation of breath from an individual. As a non-limiting example respiratory volume collection 108 may include a volume of 2.5 L of breath exhaled from an individual. As a further non-limiting example, respiratory volume collection 108 may include a volume of 0.1 L of blood from the pulmonary system of an individual. Respiratory volume collection 108 may include expired breath from any pulmonary entry and/or exit pathway, including but not limited to oral and/or nasal passages. Respiratory volume collection 108 may be received as a function of obtaining a respiratory signal from at least a sensor. As used in this disclosure "respiratory signal" is datum that relates to and/or represents an element associated with the status of an individual's respiratory system. As a non-limiting example a respiratory signal may include an image of a lung of an individual from a magnetic resonance imaging medical device. As a further non-limiting example a respiratory signal may include one or more lights, voltages, currents, sounds, chemicals, pressures, moistures, and the like thereof. Respiratory signal may include one or more respiratory biomarkers associated with the pulmonary system of an individual, wherein a biomarker is one or more chemicals, components, molecules, gases, and the like there of as described in detail below, in reference to FIG. 4. As used in this disclosure "sensor" is a device that records, monitors, stores, measures, and/or transmits respiratory signals. As a non-limiting example, a sensor may include an imaging sensor, such as optical cameras, infrared cameras, 3D cameras, multispectral cameras, hyperspectral cameras, polarized cameras, chemical sensors, motion sensors, ranging sensors, light radar component, such as lidar, detection or imaging using radio frequencies component, such as radar, terahertz or millimeter wave imagers, seismic sensors, magnetic sensors, weight/mass sensors, ionizing radiation sensors, and/or acoustical sensors. As a further non-limiting example, a sensor may include one or more medical devices that at least detect and/or monitor an individual's respiratory system, such as semi-auto analyzers, photo colorimeters, cell photo colorimeters, hemoglobin meters, mass spectrometers, chromatographic instruments, and the like thereof.

Still referring to FIG. 1, computing device 104 generates at least a respiratory parameter 112 of a plurality of respiratory parameters as a function of respiratory volume collection 108. As used in this disclosure "respiratory parameter" is a measurable value associated with an individual's respiratory system. As a non-limiting example respiratory parameter may include one or more chemical concentrations, rates of flow, lung volumes, diffusion capacities, and the like there of As a further non-limiting example a respiratory parameter may include, without limitation, an inspiratory reserve volume (IRV), tidal volume (TV), expiratory reserve volume (ERV), residual volume (RV), inspiratory capacity (IC), functional residual capacity (FRC), vital capacity (VC), total lung capacity (TLC), as described in detail below, in reference to FIG. 2. Respiratory parameter 112 is generated as a function of a respiratory algorithm 116. As used in this disclosure "respiratory algorithm" is an algorithm that determines one or more respiratory measurements. As a non-limiting example, respiratory algorithm 116 may include algorithms such as a minute ventilation, alveolar minute ventilation, airway resistance, mean airway pressure, work of breathing, alveolar-arterial oxygen tension gradient, alveolar oxygen tension, arterial/alveolar oxygen tension, arterial oxygen content, end-capillary oxygen content, mixed venous oxygen content, shunt equation, modified shunt equation, arterial-mixed venous oxygen content difference, oxygen-to-air entrainment ratio, arterial oxygen saturation estimation, P/F ratio, oxygenation index, oxygen consumption, oxygen extraction ratio, fiO2 estimation for nasal cannula, oxygen cylinder duration, liquid oxygen system duration, cardiac index, cardiac output, cardiac output Fick's method, cerebral perfusion pressure, mean arterial pressure, stroke volume, maximum heart rate, heart rate on an EKG strip, respiratory quotient, systemic vascular resistance, pulmonary vascular resistance, static compliance, dynamic compliance, dead space to tidal volume ratio, children dosage estimation, infant dosage estimation, infant and children dosage estimation, anion gap, body surface area elastance, smoking use calculation, suction catheter size estimation, endotracheal tube size estimation in children, Boyle's law, Charles' law, Gay-Lussac's law, LaPlace's law, Celsius to Fahrenheit temperature conversion, Fahrenheit to Celsius temperature conversion, Celsius to Kelvin temperature conversion, helium/oxygen conversion, total lung capacity, pressure support ventilator setting, rapid shallow breathing index, endotracheal tube size estimation in children, minimum flow rate in mechanical ventilation, and the like thereof.

Still referring to FIG. 1, computing device 104 determines a pulmonary bundle element 120 as a function of respiratory parameter 116. As used in this disclosure "pulmonary bundle element" is a profile of a user's respiratory status consisting of a group of respiratory parameters. As a non-limiting example pulmonary bundle element 120 may group respiratory parameters of oxygen saturation, cardiac index, tidal volume, and oxygen cylinder duration. Computing device 104 may determine pulmonary bundle element 120 by identifying at least a pulmonary deficiency as a function of the respiratory parameter. As used in this disclosure "pulmonary deficiency" is an inadequacy and/or deficiency of a respiratory parameter. As a non-limiting example a pulmonary deficiency may exist due to a respiratory rate of 20, wherein a respiratory rate should be 40 according to a respiratory threshold. As used in this disclosure "respiratory threshold" is a threshold a respiratory parameter should be. Respiratory threshold may be identified according to one or more medical guidelines for the measurement of respiratory function. As a non-limiting example a medical guideline for the measurement of respiratory function may include a defined threshold according to the American Association for Respiratory Care, American Medical Association, American College of Physicians, and the like thereof. As a further non-limiting example, a medical guideline for the measurement of respiratory function may include a defined threshold according to one or more medical research journals, such as the Lancet, New England Journal of Medicine, Science, Journal of the American Medical Association, and the like thereof.

Still referring to FIG. 1, computing device 104 identifies at least an edible as a function of pulmonary bundle element 120. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 identifies edible 124 as a function of obtaining a nourishment composition 128. As used in this disclosure "nourishment composition" is a list and/or compilation of all of the nutrients contained in an edible. As a non-limiting example nourishment composition 128 may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition 128 may be obtained as a function of an edible directory 132, wherein an edible directory is a database of edibles that may be identified as a function of one or more pulmonary bundle elements, as described in detail below, in reference to FIG. 3. Computing device 104 determines a nourishment deficiency 136 as a function of pulmonary bundle element 120. As used in this disclosure "nourishment deficiency" is an inadequacy and/or deficiency of a nutrient in a user's body. As a non-limiting example pulmonary bundle element 120 may determine a reduced hemoglobin concentration, wherein a nourishment deficiency may be identified as low iron. Nourishment deficiency 136 may be identified according to one or more nourishment guidelines. As a non-limiting example a nourishment guideline may be identified according to a peer-review research journal, such as the Journal of Nutrition, Nutrition and Health, Advances in Nutrition, and the like thereof.

Still referring to FIG. 1, computing device 104 identifies edible 124 as a function of nourishment composition 128, nourishment deficiency 136, and an edible machine-learning model 140. As used in this disclosure "edible machine-learning model" is a machine-learning model to produce an edible output given nourishment compositions and nourishment deficiencies as inputs; this is in contrast to a non-machine learning software program where the commands to be executed are determined in advance by a user and written in a programming language. Edible machine-learning model 140 may include one or more edible machine-learning processes such as supervised, unsupervised, or reinforcement machine-learning processes that computing device 104 and/or a remote device may or may not use in the determination of edible 124. As used in this disclosure "remote device" is an external device to computing device 104. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure a "edible training set"

is a training set that correlates at least nourishment composition and nourishment deficiency to an edible. For example, and without limitation, nourishment composition of 14 g of protein and 2 g of fiber and a nourishment deficiency of low levels of protein CC16 as a function of chronic obstructive pulmonary disease may relate to an edible of salmon. The edible training set may be received as a function of user-entered valuations of nourishment compositions, nourishment deficiencies, and/or edibles. Computing device 104 may receive edible training set by receiving correlations of nourishment compositions and/or nourishment deficiencies that were previously received and/or determined during a previous iteration of determining edibles. The edible training set may be received by one or more remote devices that at least correlate a nourishment composition and nourishment deficiency to an edible, wherein a remote device is an external device to computing device 104, as described above.

Still referring to FIG. 1, edible machine-learning model 140 may identify edible 120 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naive Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n}a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model 140 from the remote device that utilizes one or more edible machine learning processes, wherein a remote device is described above in detail. For example, and without limitation, a remote device may include a computing device, external device, processor, and the like thereof. The remote device may perform the edible machine-learning process using the edible training set to generate edible 124 and transmit the output to computing device 104. The remote device may transmit a signal, bit, datum, or parameter to computing device 104 that at least relates to edible 124. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment deficiency. Additionally or alternatively, the updated machine learning model may be transmitted to the remote device, wherein the remote device may replace the edible machine-learning model with the updated machine-learning model and determine the edible as a function of the nourishment deficiency using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may identify edible as a function of determining a pulmonary dysfunction. As used in this disclosure "pulmonary dysfunction" is an ailment and/or collection of ailments that impact an individual's respiratory system. As a non-limiting example, pulmonary dysfunctions may include asthma, chronic obstructive pulmonary disorder, chronic bronchitis, emphysema, lung cancer, cystic fibrosis, pneumonia, pleural effusion, acute bronchitis, pulmonary edema, sarcoidosis, asbestosis, autoimmune pulmonary alveolar proteinosis, Blau syndrome, bronchogenic cysts, Cantu syndrome, Gaucher disease, Henoch-Schonlein purpura, idiopathic pulmonary fibrosis, and the like thereof. Pulmonary dysfunction may be determined as a function of one or more pulmonary machine-learning models. As used in this disclosure "pulmonary machine-learning model" is a machine-learning model to produce a pulmonary dysfunction output given pulmonary bundle elements as inputs; this is in contrast to a non-machine learning software program where the commands to be executed are determined in advance by a user and written in a programming language. Pulmonary machine-learning model may include one or more pulmonary machine-learning processes such as supervised, unsupervised, or reinforcement machine-learning processes that computing device 104 and/or a remote device may or may not use in the determination of pulmonary dysfunction. As used in this disclosure "remote device" is an external device to computing device 104. A pulmonary machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train pulmonary machine-learning process as a function of a pulmonary training set. As used in this disclosure a "pulmonary training set" is a training set that correlates at least ventilatory enumeration and ventilatory effect to a pulmonary dysfunction. As used in this disclosure "ventilatory enumeration" is a measurable value associated with a ventilatory system and/or respiratory system. As used in this disclosure "ventilatory effect" is an impact and/or effect on the pulmonary system of an individual. As a non-limiting example a ventilatory enumeration of 20 may be established for a ventilatory effect of shortness of breath, wherein a pulmonary dysfunction of COVID-19 may be determined. The pulmonary training set may be received as a function of user-entered valuations of ventilatory enumerations, ventilatory effects, and/or pulmonary dysfunctions. Computing device 104 may receive pulmonary training by receiving correlations of ventilatory enumerations and/or ventilatory effects that were previously received and/or determined during a previous iteration of determining pulmonary dysfunction. The pulmonary training set may be received by one or more remote devices that correlate a ventilatory enumeration and/or ventilatory effect to a pulmonary dysfunction, wherein a remote device is an external device to computing device 104, as described above.

Still referring to FIG. 1, computing device 104 may receive pulmonary machine-learning model from the remote device that utilizes one or more pulmonary machine learning processes, wherein a remote device is described above in detail. For example, and without limitation, a remote device may include a computing device, external device, processor, and the like thereof. The remote device may perform the pulmonary machine-learning process using the pulmonary training set to generate pulmonary dysfunction and transmit the output to computing device 104.The remote device may transmit a signal, bit, datum, or parameter to computing device 104 that at least relates to pulmonary dysfunction. Additionally or alternatively, the remote device may provide an updated machine-learning model. For example, and without limitation, an updated machine-learning model may be comprised of a firmware update, a software update, a pulmonary machine-learning process correction, and the like thereof. As a non-limiting example a software update may incorporate a new ventilatory enumeration that relates to a modified ventilatory effect. Additionally or alternatively, the updated machine learning model may be transmitted to the remote device, wherein the remote device may replace the pulmonary machine-learning model with the updated machine-learning model and determine the pulmonary dysfunction as a function of the ventilatory enumeration using the updated machine-learning model. The updated machine-learning model may be transmitted by the remote device and received by computing device 104 as a software update, firmware update, or corrected pulmonary machine-learning model. For example, and without limitation pulmonary machine-learning model may utilize a logistic regression machine-learning process, wherein the updated machine-learning model may incorporate decision tree machine-learning process.

Still referring to FIG. 1, computing device 104 may identify edible as a function of a likelihood parameter. As used in this disclosure "likelihood parameter" is a parameter that identifies the probability of a user to consume an edible. As a non-limiting example likelihood parameter may identify a high probability that a user will consume an edible of steak. As a further non-limiting example likelihood parameter may identify a low probability that a user will consume an edible of cookies. Likelihood parameter may be determined as a function of a user taste profile. As used in this disclosure "user taste profile" is a profile of a user that identifies one or more desires, preferences, wishes, and/or wants that a user has. As a non-limiting example a user taste profile may include a user's preference for chicken flavor and/or crunchy textured edibles. Likelihood parameter may be determined as a function of an edible profile. As used in this disclosure "edible profile" is taste of an edible is the sensation of flavor perceived in the mouth and throat on contact with the edible. Edible profile may include one or more flavor variables. As used in this disclosure "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure "flavor directory" is a database of flavors for an edible. As a non-limiting example flavor directory may include a list and/or collection of edibles that all contain umami flavor variables. As a further non-limiting example flavor directory may include a list and/or collection of edibles that all contain sour flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 outputs a nourishment program 144 of a plurality of nourishment programs as a function of the edible 124. As used in this disclosure "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 144 may consist of recommending steak for 3 days. As a further non-limiting example nourishment program 144 may recommend chicken for a first day, spaghetti for a second day, and mushrooms for a third day. Nourishment program 144 may include one or more diet programs such as paleo, keto, vegan, vegetarian, and the like thereof. Nourishment program 144 may be outputted as a function an intended outcome. As used in this disclosure "intended outcome" is an outcome that an edible may generate according to a predicted and/or purposeful plan. As a non-limiting example, intended outcome may include a treatment outcome. As used in this disclosure "treatment outcome" is an intended outcome that is designed to at least reverse and/or eliminate the effects of the pulmonary bundle element and/or pulmonary dysfunction. As a non-limiting example, a treatment outcome may include reversing the effects of emphysema. As a further non-limiting example, a treatment outcome includes reversing the pulmonary dysfunction of lung fibrosis. Intended outcome may include a prevention outcome. As used in this disclosure "prevention outcome" is an intended outcome that is designed to at least prevent and/or avert a pulmonary bundle element and/or pulmonary dysfunction. As a non-limiting example, a prevention outcome may include preventing the development of chronic obstructive pulmonary disease.

Still referring to FIG. 1, computing device 104 may output nourishment program 144 as a function of the intended outcome using a nourishment machine-learning model. As used in this disclosure "nourishment machine-learning model" is a machine-learning model to produce a nourishment program output given edibles and/or intended outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the output of nourishment program 144. As used in this disclosure "remote device" is an external device to computing device 104. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates an intended outcome to an edible. The nourishment training set may be received as a function of user-entered edibles, intendent outcomes, and/or nourishment programs. Computing device 104 may receive nourishment training by receiving correlations of intended outcomes and/or edibles that were previously received and/or determined during a previous iteration of outputted nourishment programs. The nourishment training set may be received by one or more remote devices that correlate an intended outcome and/or edible to a nourishment program, wherein a remote device is an external device to computing device 104, as described above.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to output nourishment program 144 and transmit the output to computing device 104. The remote device may transmit a signal, bit, datum, or parameter to computing device 104 that at least relates to nourishment program 144. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new intended outcome that relates to a modified edible. Additionally or alternatively, the updated machine learning model may be transmitted to the remote device, wherein the remote device may replace the nourishment machine-learning model with the updated machine-learning model and output the nourishment program as a function of the intended outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a nearest neighbor machine-learning process, wherein the updated machine-learning model may incorporate association rules machine-learning processes.

Figure 2:
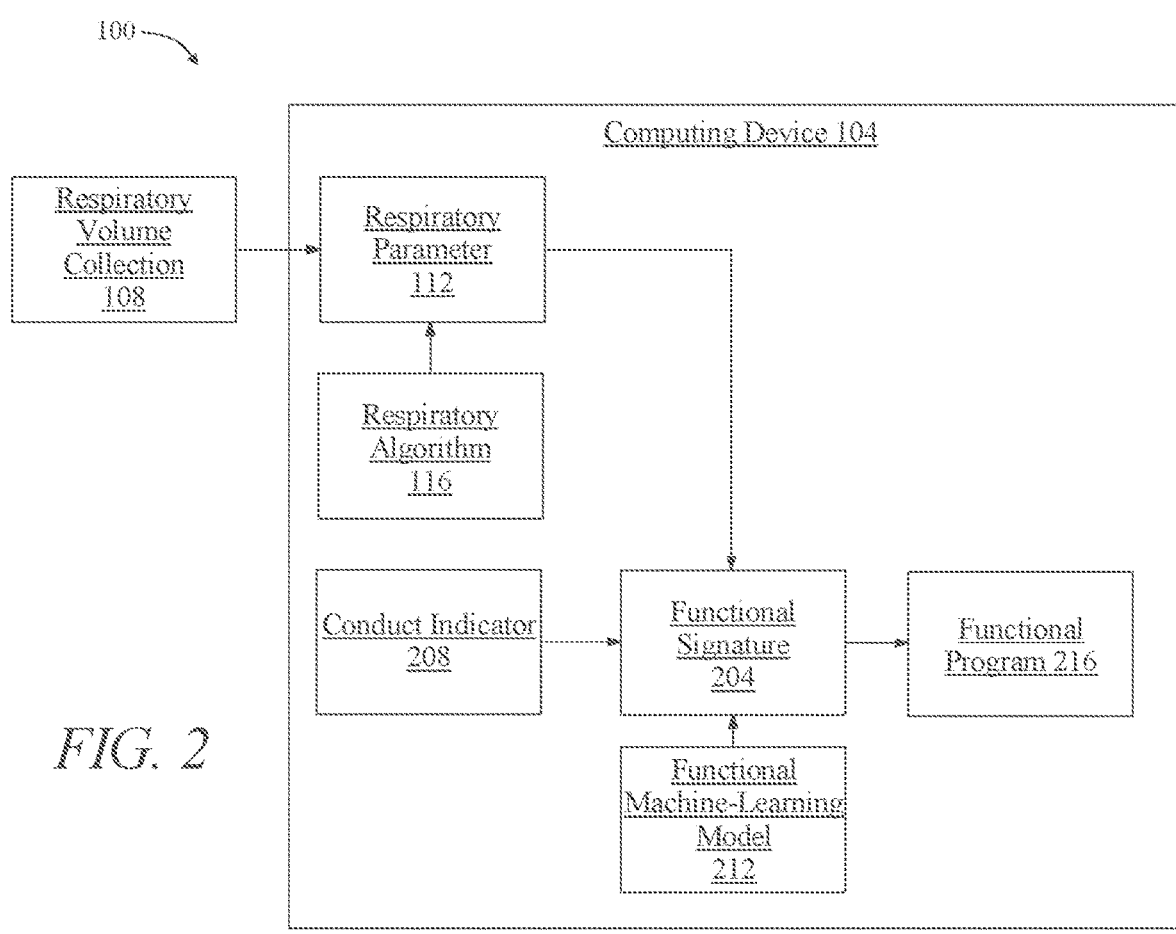
FIG. 2 is a block diagram illustrating an exemplary embodiment of a system for generating a pulmonary dysfunction functional program.

Now referring to FIG. 2, an exemplary embodiment of a system 200 for generating pulmonary dysfunction functional program is illustrated. System 200 includes computing device 104. Computing device 104 may include any computing device 104 as described above in detail, in reference to FIG. 1. For example and without limitation, computing device 104 may include a microcontroller, microprocessor, digital signal processor (DSP) and/or system on a chip (SoC) as described in this disclosure. Computing device 104 is configured to obtain a respiratory volume collection 108 relating to a user. Respiratory volume collection 108 includes any of the respiratory volume collection 108 as described above in detail, in reference to FIG. 1. For example, and without respiratory volume collection 108 may include a marker that represents a health status of a user's respiratory system such as, but not limited to a biological sample, biomarkers, respiratory signal, and the like thereof.

Still referring to FIG. 2, computing device 104 is configured to produce at least a respiratory parameter 112 of a plurality of respiratory parameters as a function of the at least a respiratory volume collection 108. Respiratory parameter 112 includes any of the respiratory parameter 112 as described above, in reference to FIG. 1. Computing device 104 generates respiratory parameter 112 using a respiratory algorithm 116. Respiratory algorithm 116 includes any of the respiratory algorithm 116 as described above, in reference to FIG. 1.

Still referring to FIG. 2, computing device 104 is configured to identify a functional signature 204 as a function of respiratory parameter 112. As used in this disclosure a "functional signature" is a profile representing an individual's relative measure of wellness. For example and without limitation, functional signature 204 may represent that an individual is "healthy" and/or in an excellent wellness state. As a further non-limiting example, functional signature 204 may represent that an individual has is "unhealthy" and/or in a poor wellness state. In an embodiment, and without limitation, computing device 104 may identify functional signature 204 as a function of determining a pulmonary dysfunction, wherein determining a pulmonary dysfunction is described above, in reference to FIG. 1. Pulmonary dysfunction includes any of the pulmonary dysfunction as described above, in reference to FIG. 1. Functional signature 204 is identified as a function of receiving a conduct indicator 208. As used in this disclosure a "conduct indicator" is an element of data denoting an individual's lifestyle choices. In an embodiment conduct indicator 208 may include one or more biological, psychological, social, and/or spiritual elements. For example, and without limitation, conduct indicator 208 may denote a biological element, wherein the biological indicator may denote that an individual has low cholesterol and/or exercises frequently. As a further non-limiting example, conduct indicator 208 may denote a psychological element, wherein the psychological element may denote that an individual is happy and/or content. As a further non-limiting example, conduct indicator 208 may denote a social element, wherein the social element may indicate that an individual has 36 friends. As a further non-limiting example, conduct indicator 208 may denote a spiritual element, wherein the spiritual element may indicate that an individual belongs to the Hinduism religion. As a further non-limiting example, spiritual element may denote one or more chakras and/or spiritual energies of an individual. In an embodiment conduct indicator 208 may denote one or more lifestyles groups such as, but not limited to, general lifestyles, income, profession, and/or occupation lifestyles, consumption-based lifestyles, social and/or political lifestyles, marketing lifestyles, military lifestyles, sexual lifestyles, spiritual lifestyles, religious lifestyles, musical lifestyles, recreational lifestyles, and the like thereof. For example, and without limitation, lifestyles may include activism, asceticism, modern primitivism, bohemianism, communal living, clothes free, groupie lifestyle, hippie, quirkyalone, rural lifestyle, simple living, traditional lifestyle, criminality, farming, jet set, piracy, poverty, prostitution, sarariman, workaholic, yuppie, social liberalism, social conservatism, polygamy, monogamy, ahimsa, Hinduism, Christianity, evangelicalism, Islam, Judaism, missionary, Zen, yoga, Thelema, surfer, athleticism, hunter, artist, golf, recreational drug use, and the like thereof. Additionally or alternatively conduct indicator 208 may include one or more markers associated with an individual's behavior such as, but not limited to, markers identified respiratory volume collection 108. For example, and without limitation markers may include but are not limited to biological samples, biomarkers, respiratory signals, and the like thereof as defined above, in reference to FIG. 1.

Still referring to FIG. 2, conduct indicator 208 may include a dimensional element. As used in this disclosure a "dimensional element" is an element of datum denoting a relative measure of wellness of an individual. For example, and without limitation dimensional element may denote one or more dimensions associated with healthy living. In an embodiment dimensional element may include an occupational dimension. As used in this disclosure an "occupational dimension" is a dimension of wellness representing personal satisfaction and enrichment in an individual's life through work and/or occupation. For example, and without limitation, occupational dimension may denote that an individual's job is rewarding due to the contribution of personal values, interests, and/or beliefs that are shared among the job and the individual. In an embodiment dimensional element may include a physical dimension. As used in this disclosure a "physical dimension" is a dimension of wellness representing physical activity and/or nutrition. For example, and without limitation, physical dimension may include a dimension associated with eating whole grain foods and/or lean protein foods diet and/or nutrition, while concurrently discouraging the use of recreational drugs. As a further non-limiting example, physical dimension may include a dimension associated with regular exercise and/or enhanced physical strength. In an embodiment dimensional element may include a social dimension. As used in this disclosure a "social dimension" is a dimension of wellness representing an individual's contributions towards the environment and/or community. For example, and without limitation, social dimension may include a dimension associated with an individual's contributions towards the common welfare of the community and./or living in harmony with other.

In an embodiment and still referring to FIG. 2, dimensional element may include an intellectual dimension. As used in this disclosure a "intellectual dimension" is a dimension of wellness representing an individual's creative and/or mental activities. For example, and without limitation, intellectual dimension may include a dimension associated with an individual's abilities to identify potential problems and choose appropriate courses of action based on available information than to wait, worry, and contend with major concerns later. In an embodiment dimensional element may include a spiritual dimension. As used in this disclosure a "spiritual dimension" is a dimension of wellness representing an individual's search for meaning and/or purpose of existence. For example, and without limitation, spiritual dimension may include a dimension associated with an individual's understanding of the meaning for existence and/or the tolerance of other's meaning for existence. In an embodiment dimensional element may include an emotional dimension. As used in this disclosure an "emotional dimension" is a dimension of wellness representing an individual's awareness and/or acceptance of feelings. For example, and without limitation, emotional dimension may include a dimension associated with an individual's feelings related to a belief, philosophy, behavior, and the like thereof.

Still referring to FIG. 2, computing device 104 may receive conduct indicator 208 as a function of obtaining an exposure element. As used in this disclosure an "exposure element" is an element of datum representing contact and/or exposure associated with a lifestyle. For example, and without limitation exposure element may denote prolonged contact to radioactive material as a function of being a nuclear power plant technician. As a further non-limiting example exposure element may denote prolonged contact to illicit drugs as a function of being a recreational drug user. As a further non-limiting example, exposure element may denote prolonged contact to heavy metals in water as a function of having a surfing lifestyle. In an embodiment, and without limitation, exposure element may denote one or more exposures to toxins such as, but not limited to, persistent organic pollutants, polychlorinated bisphenols, hydrogen chlorides, benzenes, xylenes, toluenes, dioxins, heavy metals, radioactivity, and the like thereof. In another embodiment, exposure element may denote one or more epigenetic factors. As used in this disclosure an "epigenetic factor" is a factor denoting a likelihood of a change in gene activity and/or expression as a function of one or more external factors. For example, and without limitation, epigenetic factor may denote a high likelihood for a gene mutation as a function of a polyaromatic hydrocarbon. As a further non-limiting example, epigenetic factor may denote a high likelihood for reduced gene expression as a function of aluminum toxicity and/or poisoning.

In an embodiment, and still referring to FIG. 2, functional signature 204 may be obtained as a function of obtaining a salubrious reference. As used in this disclosure a "salubrious reference" is a guideline and/or recommendation representing an ideal health level of an individual. For example, and without limitation salubrious reference may include a guideline that a blood pressure should be 120/80 mmHg. As a further non-limiting example, salubrious reference may include a recommendation that a respiratory rate should be 14 breaths per minute. As a further non-limiting example, salubrious reference may denote that an individual should exercise for 30 minutes every other day. As a further non-limiting example, salubrious reference may denote that an individual should attend a religious gathering once a week. As a further non-limiting example, salubrious reference may denote that an individual should meditate twice a day for 10 minutes. As a further non-limiting example, salubrious reference may denote that an individual should have 5 or more chakras balanced during a particular time period, wherein a time period includes milliseconds, seconds, minutes, hours, days, weeks, months, years, and the like thereof. Salubrious reference may be obtained as a function of one or more informed advisors, wherein an informed advisor is described above in detail. Additionally or alternatively, salubrious reference may be obtained as a function of one or more functional advisors. As used in this disclosure a "functional advisor" is an individual capable of recommending and/or guiding an individual towards a more suited wellness state. For example, and without limitation, functional advisor may include one or more nutritionists, personal trainers, physical therapists, spiritual leaders, religious leaders, massage therapists, spiritual therapists, reiki masters, acupuncturists, life coaches, priests, philosophers, theologists, yoga instructors, wellness instructors, teachers, and the like thereof. In an embodiment, salubrious reference may include recommendations from one or more medical sources such as peer reviews, informed advisor associations, medical websites, medical textbooks, religious books, prophecies, spiritual texts, and the like thereof.

Still referring to FIG. 2, computing device 104 identifies functional signature 204 as function of conduct indicator 208 and respiratory parameter 112 using a functional machine-learning model 212. As used in this disclosure a "functional machine-learning model" is a machine-learning model that identifies a functional signature output given respiratory parameters and conduct indicators as inputs; this is in contrast to a non-machine learning software program where the commands to be executed are determined in advance by a user and written in a programming language. Functional machine-learning model may include one or more functional machine-learning processes such as supervised, unsupervised, or reinforcement machine-learning processes that computing device 104 and/or a remote device may or may not use in the determination of functional signature 204, wherein a remote device is an external device to computing device 104 as described above in detail. A functional machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naive bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train functional machine-learning process as a function of a functional training set. As used in this disclosure a "functional training set" is a training set that correlates a respiratory parameter and a conduct indicator to a functional signature. For example, and without limitation, a respiratory parameter of reduced tidal volume and a conduct indicator associated with smoking cigarettes for 20 years may relate to a functional signature of a relatively "unhealthy" wellness state. The functional training set may be received as a function of user-entered valuations of respiratory parameters, conduct indicators, and/or functional signatures. Computing device 104 may receive functional training set by receiving correlations of respiratory parameters and/or conduct indicators that were previously received and/or determined during a previous iteration of determining functional signatures. The functional training set may be received by one or more remote devices that at least correlate a respiratory parameter and conduct indicator to a functional signature, wherein a remote device is an external device to computing device 104, as described above. Functional training set may be received in the form of one or more user-entered correlations of a respiratory parameter and/or conduct indicator to a functional signature. Additionally or alternatively, a user may include, without limitation, an informed advisor and/or a functional advisor entering correlations of respiratory parameters and/or conduct indicators to functional signatures, wherein informed advisors and/or functional advisors may include, without limitation, physicians, nutritionists, therapists, spiritual leaders, and the like thereof as described above in detail.

Still referring to FIG. 2, computing device 104 may receive functional machine-learning model 212 from a remote device that utilizes one or more functional machine learning processes, wherein remote device is described above in detail. For example, and without limitation, remote device may include a computing device, external device, processor, and the like thereof. Remote device may perform the functional machine-learning process using the functional training set to generate functional signature 204 and transmit the output to computing device 104. Remote device may transmit a signal, bit, datum, or parameter to computing device 104 that at least relates to functional signature 204. Additionally or alternatively, the remote device may provide an updated machine-learning model. For example, and without limitation, an updated machine-learning model may be comprised of a firmware update, a software update, a functional machine-learning process correction, and the like thereof. As a non-limiting example a software update may incorporate a new respiratory parameter that relates to a modified conduct indicator. Additionally or alternatively, the updated machine learning model may be transmitted to the remote device, wherein the remote device may replace the functional machine-learning model with the updated machine-learning model and determine the physiological as a function of the conduct indicator using the updated machine-learning model. The updated machine-learning model may be transmitted by the remote device and received by computing device 104 as a software update, firmware update, or corrected functional machine-learning model. For example, and without limitation a functional machine-learning model 212 may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, functional machine-learning model 212 may identify functional signature 204 as a function of one or more classifiers, wherein a classifier is described above in detail.

Still referring to FIG. 2, computing device 104 may identify functional signature 204 by producing an indicator index as a function of conduct indicator 208. As used in this disclosure an "indicator index" is a measurable value associated with a conduct indicator. For example and without limitation, an indicator index may be 20 for a conduct indicator associated with meditating 3 times a day for 5 minutes. As a further non-limiting example, an indicator index may be 73 for a conduct indicator associated with a sedentary lifestyle comprising sitting down for 12 hours a day. In an embodiment, computing device may produce a weighted index as a function of the indicator index and pulmonary dysfunction. As used in this disclosure a "weighted index" is a weighted value associated with conduct indicator and pulmonary dysfunction. For example, and without limitation, a conduct indicator of a lifestyle of smoking tobacco for 30 years may relate to a value of 18, wherein a pulmonary dysfunction for COPD may weight and/or alter the value to adjust to 73.

Still referring to FIG. 2, computing device 104 may identify functional signature 204 as a function of determining a root cause. As used in this disclosure a "root cause" is a source of origination of a conduct indicator. For example, and without limitation, root cause may denote that an individual has a sedentary lifestyle as a function of watching television. As a further non-limiting root cause may denote that an individual started smoking as a function of a lack of religious guidance and/or spiritual teaching. As a further non-limiting example, root cause may denote that an individual has emotional instability as a function of one or more traumatic experiences and/or psychological traumas. Additionally or alternatively, computing device 104 may determine a habit as a function of conduct indicator 208. As used in this disclosure a "habit" is a tendency and/or regularly practiced behavior that an individual performs. For example, and without limitation a habit may include swearing, trichotillomania, picking an individual's nose, smoking cigarettes, biting fingernails, drinking coffee, drinking tea, hair picking, watching television, eating fast food, alcohol, emotional shopping, social media use, drinking soda, eating chocolate, humming, sleeping-in, lying, procrastinating, being unfriendly, and the like thereof.

Still referring to FIG. 2, computing device 104 is configured to generate a functional program 216 as a function of functional signature 204. As used in this disclosure a "functional program" is a program and/or instruction set to alter an individual's lifestyle to affect respiratory parameter 112 and/or functional signature 204. A functional program may provide instruction relating to one or more areas of a user's life, including but not limited to, physical fitness, stress management, meditation, spirituality, religion, energy healing, professional endeavors, personal endeavors, body, mind, health, finances, recreation, romance, personal development, and the like. For example, and without limitation, functional program 216 may include a program that instructs an individual to perform 10 minutes of strenuous exercise every day for 5 weeks. As a further non-limiting example, functional program 216 may include a program that instructs an individual to meditate for 1 minute every other week. As a further non-limiting example, functional program 216 may instruct an individual to go on a hike for 2 hours once a week. Additionally or alternatively, functional program 216 may include a nourishment program 144, wherein nourishment program 144 is described above in detail, in reference to FIG. 1. For example, and without limitation, functional program 216 may instruct an individual to consume a paleo diet. In an embodiment and without limitation, functional program 216 may include one or more instructions such as, but not limited to a first instruction to exercise and a second instruction of a nourishment program. Computing device 104 may functional program 216 as a function of functional signature 204 using a program machine-learning model. As used in this disclosure a "program machine-learning model" is a machine-learning model that produces a functional program output given functional signatures as inputs; this is in contrast to a non-machine learning software program where the commands to be executed are determined in advance by a user and written in a programming language. Program machine-learning model may include one or more program machine-learning processes such as supervised, unsupervised, or reinforcement machine-learning processes that computing device 104 and/or a remote device may or may not use in the determination of functional program 216, wherein a remote device is an external device to computing device 104 as described above in detail. A program machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train program machine-learning process as a function of a program training set. As used in this disclosure a "program training set" is a training set that correlates a functional signature to a functional program. For example, and without limitation, a functional signature of a habit of being exposed to radioactivity may relate to a functional program of a reduced exposure to radioactivity, exercise for 30 minutes to aid in eliminating the toxin, and increased meditation to reduce inflammation. The program training set may be received as a function of user-entered valuations of functional signatures, and/or functional programs. Computing device 104 may receive program training set by receiving correlations of functional signatures that were previously received and/or determined during a previous iteration of determining functional programs. The program training set may be received by one or more remote devices that at least correlate a functional signature to a functional program, wherein a remote device is an external device to computing device 104, as described above. Program training set may be received in the form of one or more user-entered correlations of a functional signature to a functional program. Additionally or alternatively, a user may include, without limitation, an informed advisor and/or a functional advisor entering correlations of functional signatures to functional programs, wherein informed advisors and/or functional advisors may include, without limitation, physicians, nutritionists, therapists, spiritual leaders, and the like thereof as described above in detail.

Still referring to FIG. 2, computing device 104 may receive program machine-learning model from a remote device that utilizes one or more program machine learning processes, wherein remote device is described above in detail. For example, and without limitation, remote device may include a computing device, external device, processor, and the like thereof. Remote device may perform the program machine-learning process using the program training set to generate functional program 216 and transmit the output to computing device 104. Remote device may transmit a signal, bit, datum, or parameter to computing device 104 that at least relates to functional program 216. Additionally or alternatively, the remote device may provide an updated machine-learning model. For example, and without limitation, an updated machine-learning model may be comprised of a firmware update, a software update, a program machine-learning process correction, and the like thereof. As a non-limiting example a software update may incorporate a new functional signature that relates to a modified functional program. Additionally or alternatively, the updated machine learning model may be transmitted to the remote device, wherein the remote device may replace the program machine-learning model with the updated machine-learning model and determine the functional program as a function of the functional signature using the updated machine-learning model. The updated machine-learning model may be transmitted by the remote device and received by computing device 104 as a software update, firmware update, or corrected program machine-learning model. For example, and without limitation a program machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, program machine-learning model may identify functional program 216 as a function of one or more classifiers, wherein a classifier is described above in detail.

Still referring to FIG. 2, computing device 104 may generate functional program 216 as a function of determining a holistic prospect. As used in this disclosure a "holistic prospect" is a potential adjustment to an individual's functional signature. For example, and without limitation, holistic project may denote that a potential adjustment may include adjusting the amount of exercise and/or strenuous activity performed by the individual. As a further non-limiting example, holistic project may denote that a potential adjustment may include adjusting the amount of religious guidance that an individual receives. As a further non-limiting example, holistic project may denote that a potential adjustment may include adjusting the amount of chakra flow of an individual. As a further non-limiting example, holistic project may denote that a potential adjustment may include adjusting the number of social interactions that an individual experiences each day. As a further non-limiting example, holistic prospect may include a potential adjustment to a nourishment program through the alteration of one or more edibles and/or supplementation of a nourishment program. In an embodiment, holistic prospect may include one or more supplements. For example, and without limitation, a supplement may include vitamin E, linoleic acid, lipoic acid, inositol, magnesium, biotin, progestin, vitamin D, and the like thereof.

Still referring to FIG. 2, computing device 104 generate functional program 216 as a function of a pulmonary functional goal. As used in this disclosure an "pulmonary functional goal" is a predicted goal and/or purposeful plan to modify functional signature 204 and/or respiratory parameter 112. As a non-limiting example, pulmonary functional goal may include a treatment goal. As used in this disclosure a "treatment goal" is a pulmonary functional goal that is designed to at least reverse and/or eliminate functional signature 204, respiratory parameter 112, and/or pulmonary dysfunction. As a non-limiting example, a treatment goal may include reversing the effects of COPD as a function of exercise, diet, and/or supplementation. As a further non-limiting example, a treatment goal includes reversing SARS-CoV-2 as a function of recommending the supplement N-acetyl cysteine, recommending edibles such as apples, berries, tomatoes, celery, onions, sauerkraut, kombucha, and the like thereof, recommending a meditation schedule of once per day for 20 minutes, and/or recommending 25 minutes of exercise every other day. Pulmonary functional goal may include a prevention goal. As used in this disclosure a "prevention goal" is a pulmonary functional goal that is designed to at least prevent and/or avert functional signature 204, respiratory parameter 112, and/or pulmonary dysfunction. As a non-limiting example, a prevention goal may include preventing the development of the asthma as a function of hiking 2 miles per day and/or recommending a nourishment program of a low-carb diet. Pulmonary functional goal may include a mitigation goal. As used in this disclosure a "mitigation goal" is a functional goal that is designed to reduce the symptoms and/or effects of a pulmonary dysfunction. For example, and without limitation, mitigation goal may include reducing the effects of lung cancer as a function of recommending magnesium and/or zinc supplements and/or recommending enhanced chakra flow of an individual's body. Additionally or alternatively, pulmonary functional goal may include one or more goals associated with gene therapy to alter and/or mutate an individual's epigenetic factors.

Still referring to FIG. 2, computing device 104 may generate functional program 216 as a function of functional signature 204 and pulmonary functional goal using a goal machine-learning model. As used in this disclosure a "goal machine-learning model" is a machine-learning model to produce a functional program output given functional signatures and/or pulmonary functional goals as inputs; this is in contrast to a non-machine learning software program where the commands to be executed are determined in advance by a user and written in a programming language. Goal machine-learning model may include one or more goal machine-learning processes such as supervised, unsupervised, or reinforcement machine-learning processes that computing device 104 and/or a remote device may or may not use in the development of functional program 216. Goal machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train goal machine-learning process as a function of a goal training set. As used in this disclosure a "goal training set" is a training set that correlates a pulmonary functional goal to a functional signature. The goal training set may be received as a function of user-entered functional signatures, pulmonary functional goals, and/or functional programs. For example, and without limitation, a pulmonary functional goal of treating emphysema may correlate to a functional signature of physical activity and/or a vegan diet. Computing device 104 may receive goal training by receiving correlations of pulmonary functional goals and/or functional signatures that were previously received and/or determined during a previous iteration of generating functional programs. The goal training set may be received by one or more remote devices that at least correlate a pulmonary functional goal and/or functional signature to a functional program, wherein a remote device is an external device to computing device 104, as described above. Goal training set may be received in the form of one or more user-entered correlations of a pulmonary functional goal and/or functional signature to a functional program. Additionally or alternatively, a user may include, without limitation, an informed advisor and/or a functional advisor entering correlations of functional signatures and/or pulmonary appraisals to functional programs, wherein informed advisors and/or functional advisors may include, without limitation, physicians, nutritionists, therapists, spiritual leaders, and the like thereof as described above in detail.

Still referring to FIG. 2, computing device 104 may receive goal machine-learning model from the remote device that utilizes one or more goal machine learning processes, wherein a remote device is described above in detail. For example, and without limitation, a remote device may include a computing device, external device, processor, and the like thereof. The remote device may perform the goal machine-learning process using the goal training set to develop functional program 216 and transmit the output to computing device 104. The remote device may transmit a signal, bit, datum, or parameter to computing device 104 that at least relates to functional program 216. Additionally or alternatively, the remote device may provide an updated machine-learning model. For example, and without limitation, an updated machine-learning model may be comprised of a firmware update, a software update, a goal machine-learning process correction, and the like thereof. As a non-limiting example a software update may incorporate a new pulmonary functional goal that relates to a modified functional signature. Additionally or alternatively, the updated machine learning model may be transmitted to the remote device, wherein the remote device may replace the goal machine-learning model with the updated machine-learning model and develop the functional program as a function of the pulmonary functional goal using the updated machine-learning model. The updated machine-learning model may be transmitted by the remote device and received by computing device 104 as a software update, firmware update, or corrected goal machine-learning model. For example, and without limitation goal machine-learning model may utilize a neural net machine-learning process, wherein the updated machine-learning model may incorporate decision tree machine-learning processes.

Figure 3:
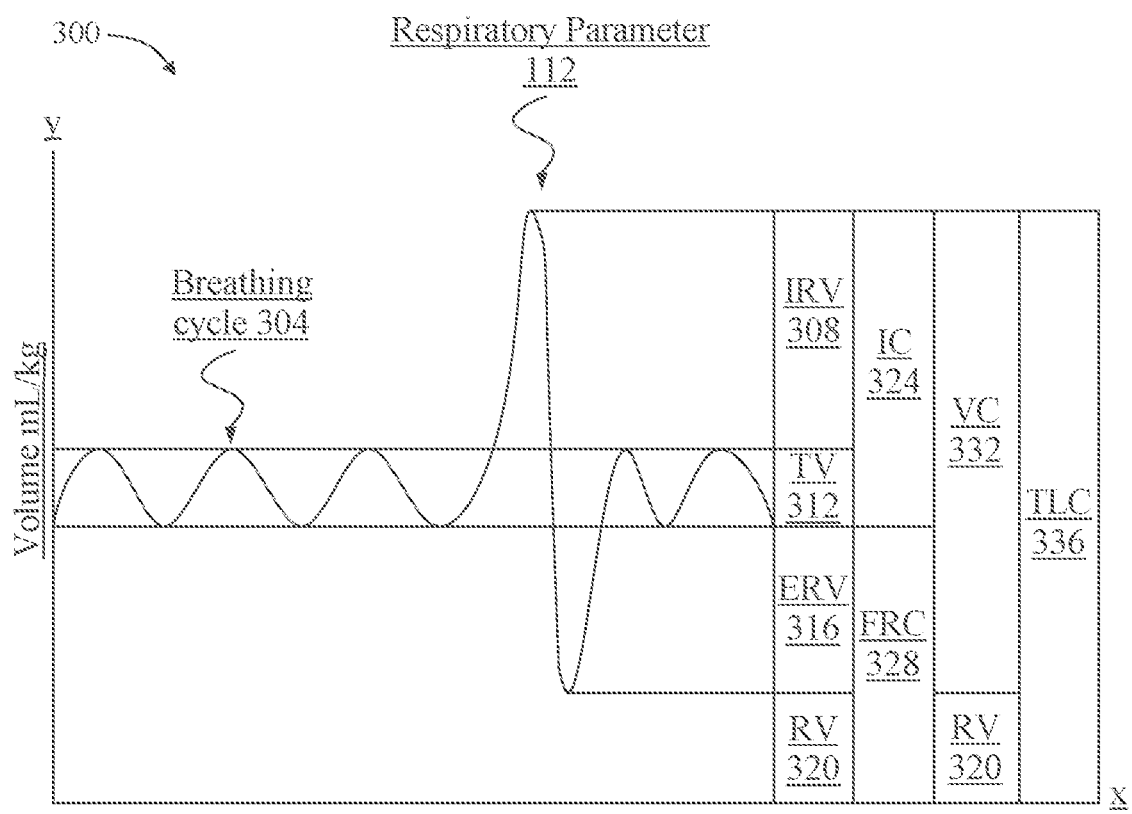
FIG. 3 is a representative diagram of an exemplary embodiment of respiratory parameters according to an embodiment of the invention.

Now referring to FIG. 3, an exemplary embodiment 300 of a representative diagram of respiratory parameter 112 according to an embodiment of the invention is illustrated. Respiratory parameter 112 may include one or more respiratory measurements according to a breathing cycle 304. As used in this disclosure "breathing cycle" is the movement of air during both inhalation and exhalation, wherein inhalation is represented as an increase along a y-axis representing volume in mL/kg and exhalation is represented as a decreases along a x-axis representing time. Breathing cycle 304 may represent both regulatory breathing, wherein the individual is not participating in any strenuous respiratory activities and/or strenuous breathing, wherein the individual is inhaling air in an attempt to maximize the inhalation and exhaling the maximum amount of air that was inhaled. Respiratory parameter 112 may include an inspiratory reserve volume (IRV) 308 as a function of breathing cycle 304. As used in this disclosure "inspiratory reserve volume (IRV)" is the additional amount of air that can be inhaled after a normal inhalation. As a non-limiting example IRV 308 may include an individual that may normally inhale 2 L of air, wherein an additional 1.5 L of air may be additionally inhaled. Respiratory parameter 112 may include a tidal volume (TV) 312 as a function of breathing cycle 304. As used in this disclosure "tidal volume (TV)" is the amount of air that is inspired and expired during a normal breath. As a non-limiting example, TV 312 may include an individual that normally inhales and exhales 1 L of air. Respiratory parameter 112 may include calculating an expiratory reserve volume (ERV) 316 as a function of breathing cycle 304. As used in this disclosure "expiratory reserve volume (ERV)" is the additional amount of air that can be exhaled after a normal exhalation. As a non-limiting example, ERV 316 may include an individual that may normally exhale 1 L of air, wherein an additional 2.5 L of air may be additionally exhaled. Respiratory parameter 112 may include a residual volume (RV) 320 as a function of breathing cycle 304. As used in this disclosure "residual volume (RV)" is the additional amount of air that is left after ERV is exhaled. As a non-limiting example, RV 320 may include an individual that has exhaled 2.5 L of ERV, wherein 1.25 L of air remains in the lungs of the individual.

Still referring to FIG. 3, respiratory parameter 112 may include inspiratory capacity (IC) 324 as a function of breathing cycle 304. As used in this disclosure "inspiratory capacity (IC)" is the amount of air that may be inhaled after the end of a normal expiration. As a non-limiting example IC 324 may include a total volume of 3.25 L that may be inhaled after an individual has normally exhaled. Respiratory parameter 112 may include functional residual capacity (FRC) 328. As used in this disclosure "functional residual capacity (FRC)" is the amount of additional air that can be exhaled after a normal exhalation. As a non-limiting example FRC 328 may include a total volume of 2.75 L that may be exhaled after an individual has normally inhaled. Respiratory parameter 112 may include vital capacity (VC) 332. As used in this disclosure "vital capacity (VC)" is the maximum amount of air that can be inhaled or exhaled during a respiratory cycle. As a non-limiting example VC 332 may be the sum of ERV, TV, and IRV to determine a maximum amount of air that may be inhaled and/or exhaled by an individual. Respiratory parameter 112 may include a total lung capacity (TLC) 336. As used in this disclosure "total lung capacity (TLC)" is the total amount of air that an individual's lung may hold. As a non-limiting example TLC 336 may the sum of RV, ERV, TV, and IRV to determine a total amount of air that an individual's lung may hold.

Figure 4:
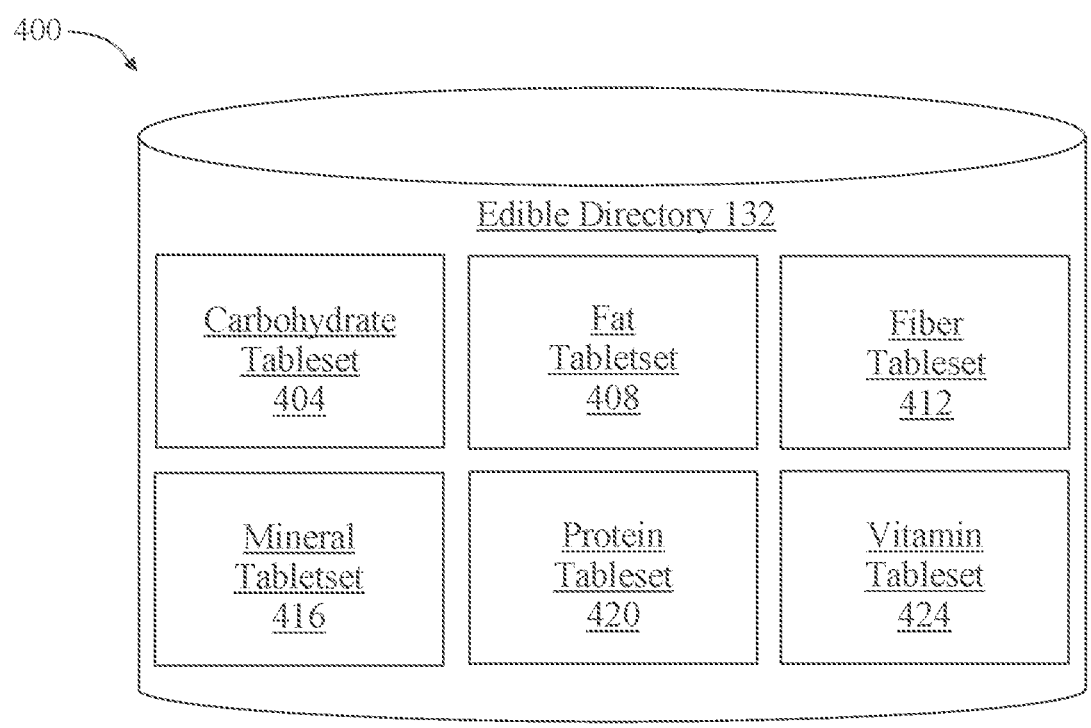
FIG. 4 is a block diagram of an exemplary embodiment of an edible directory according to an embodiment of the invention.

Now referring to FIG. 4, an exemplary embodiment 400 of an edible directory 132 according to an embodiment of the invention is illustrated. Edible directory 132 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 132 may alternatively or additionally be implemented using a distributed data storage protocol and/or data structure, such as a distributed hash table or the like. Edible directory 132 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 132 may include a carbohydrate tableset 404. Carbohydrate tableset 404 may relate to a nourishment composition of an edible with respect to the quantity and/or type of carbohydrates in the edible. As a non-limiting example, carbohydrate tableset 404 may include monosaccharides, disaccharides, oligosaccharides, polysaccharides, and the like thereof. Edible directory 132 may include a fat tableset 408. Fat tableset 408 may relate to a nourishment composition of an edible with respect to the quantity and/or type of esterified fatty acids in the edible. Fat tableset 408 may include, without limitation, triglycerides, monoglycerides, diglycerides, phospholipids, sterols, waxes, and free fatty acids. Edible directory 132 may include a fiber tableset 412. Fiber tableset 412 may relate to a nourishment composition of an edible with respect to the quantity and/or type of fiber in the edible. As a non-limiting example, fiber tableset 412 may include soluble fiber, such as beta-glucans, raw guar gum, psyllium, inulin, and the like thereof as well as insoluble fiber, such as wheat bran, cellulose, lignin, and the like thereof. Edible directory 132 may include a mineral tableset 416. Mineral tableset 416 may relate to a nourishment composition of an edible with respect to the quantity and/or type of minerals in the edible. As a non-limiting example, mineral tableset 416 may include calcium, phosphorous, magnesium, sodium, potassium, chloride, sulfur, iron, manganese, copper, iodine, zing, cobalt, fluoride, selenium, and the like thereof. Edible directory 132 may include a protein tableset 420. Protein tableset 420 may relate to a nourishment composition of an edible with respect to the quantity and/or type of proteins in the edible. As a non-limiting example, protein tableset 420 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 132 may include a vitamin tableset 424. Vitamin tableset 424 may relate to a nourishment composition of an edible with respect to the quantity and/or type of vitamins in the edible. As a non-limiting example, vitamin tableset 424 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 5:
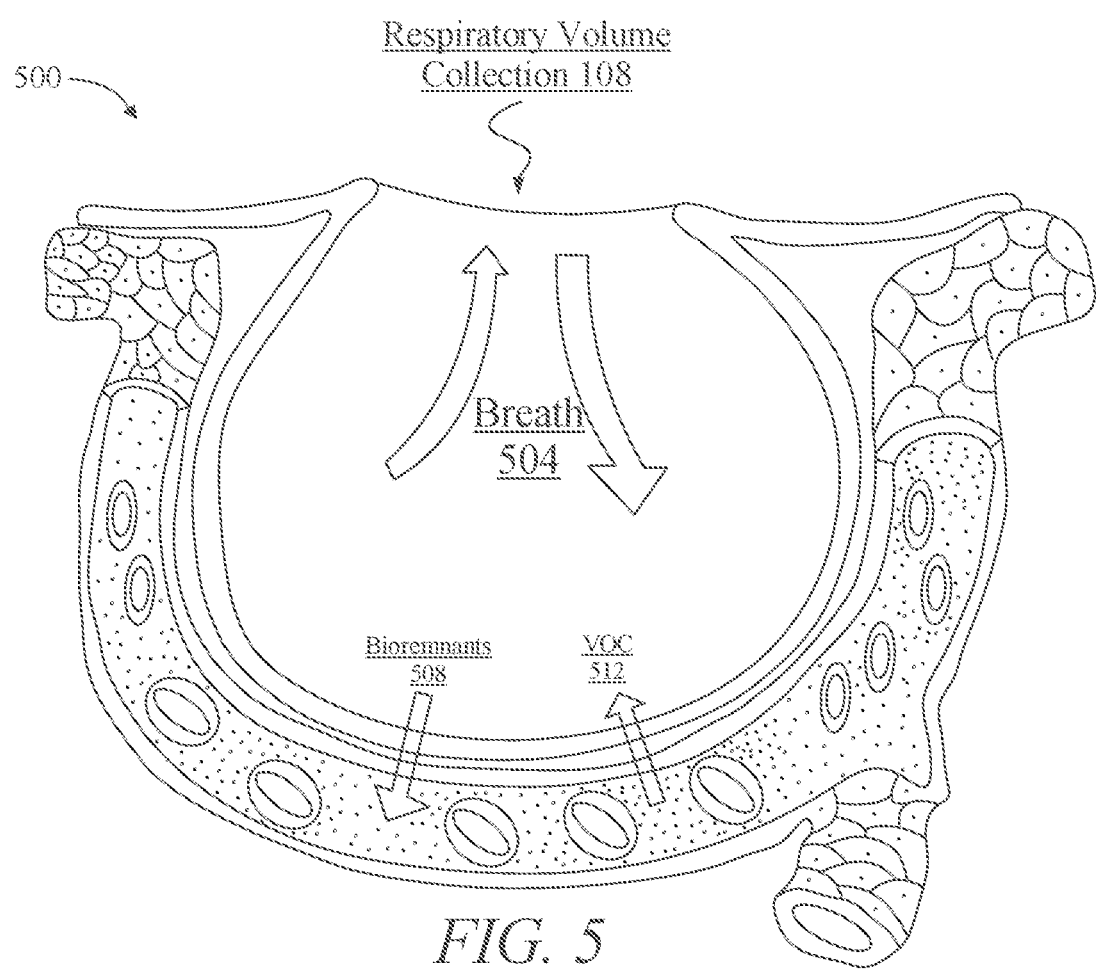
FIG. 5 is a representative diagram of an exemplary embodiment of biomarkers that can be received from a respiratory volume collection according to an embodiment of the invention.

Now referring to FIG. 5 an exemplary embodiment 500 of biomarkers that may be received from respiratory volume collection 108 is illustrated. Respiratory volume collection 108 may collect a breath 504. As used in this disclosure "breath" is air that is taken into and/or expelled from the lungs, wherein the air interacts with one or more alveolus of the lung. Breath 504 may include one or more chemical elements such as nitrogen, oxygen, argon, carbon dioxide, neon, helium, and/or hydrogen. As a non-limiting example, breath 504 may be comprised of 78% of nitrogen, 20.95% of oxygen, and 1.05% of neon. As a further non-limiting example, breath 504 may be comprised of 78% nitrogen, 16% oxygen, 1% argon, and 5% carbon dioxide. Breath 504 may contain a bioremnant 508. As used in this disclosure "bioremnant" is a biological component that originates from an individual's body that represents the status of an individual's respiratory system. As a non-limiting example bioremnant 508 may include a biological component such as a Lung function, Alpha1-antitrypsin (AAT), angiogenic growth factor, brain natriuretic peptide (BNP), calprotectin, CF-specific serum proteomic signature, chromagranim A (CgA), copeptin, C-reactive protein (CRP), IgE, Nitric oxide, osteoprotegerin, parathyroid hormone, serum amyloid A, surfactant proteins, and the like thereof. Breath 504 may include a volatile organic compound (VOC) 512. As used in this disclosure "volatile organic compound (VOC)" is an organic compound that has a high vapor pressure that allows the organic compound to evaporate and/or sublime at room temperature. VOC 512 may include one or more biologically generated VOCs, wherein biologically generated VOCs may include, without limitation, isoprene, terpenes, pinene isomers, sesquiterpenes, methanol, acetone, and the like thereof. As a non-limiting example VOC 512 may include benzene, ethylene glycol, formaldehyde, methylene chloride, tetrachloroethylene, toluene, xylene, 1,3-butadiene, and the like thereof.

Figure 6:
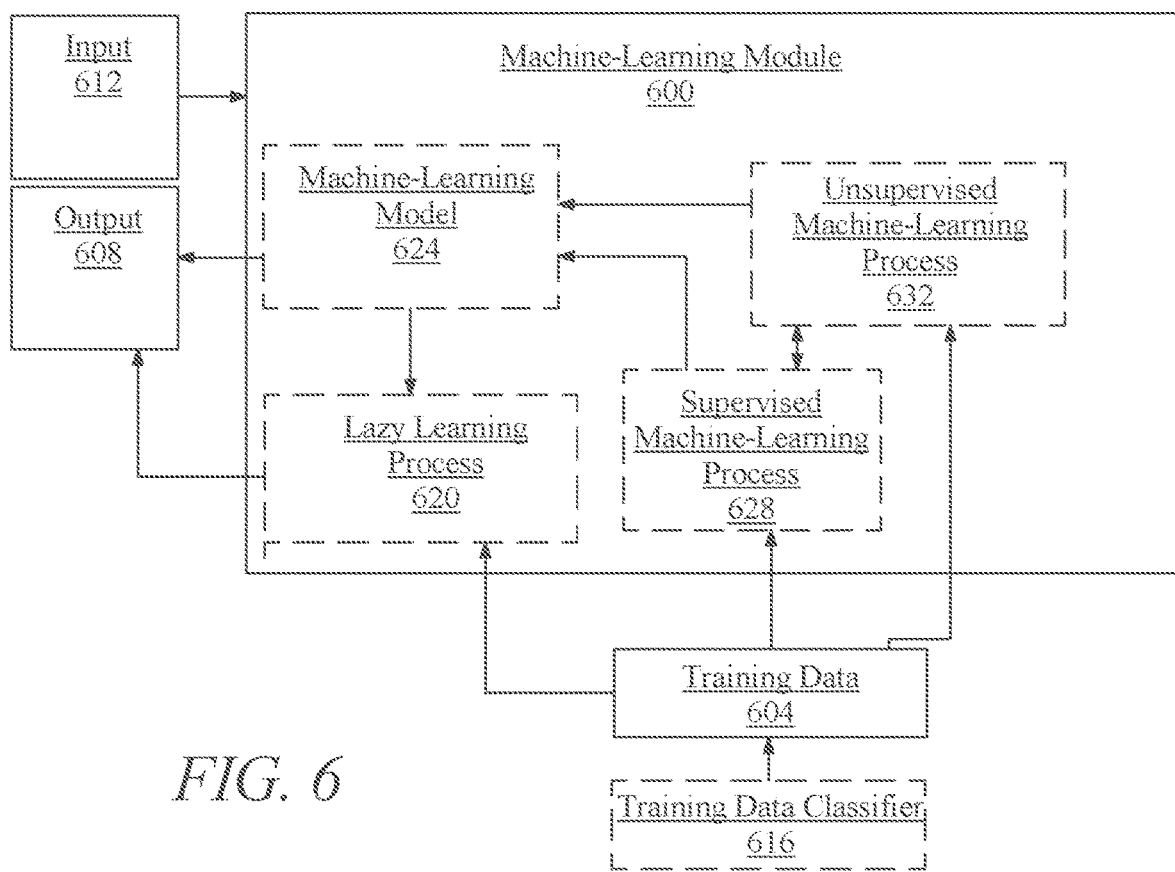
FIG. 6 is a block diagram of an exemplary embodiment of a machine-learning module.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example nourishment compositions and nourishment deficiencies may be inputs, wherein an edible is outputted.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to classes of deficiencies, wherein a nourishment deficiency may be categorized to a large deficiency, a medium deficiency, and/or a small deficiency.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include nourishment compositions and/or nourishment deficiencies as described above as inputs, edibles as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 7:
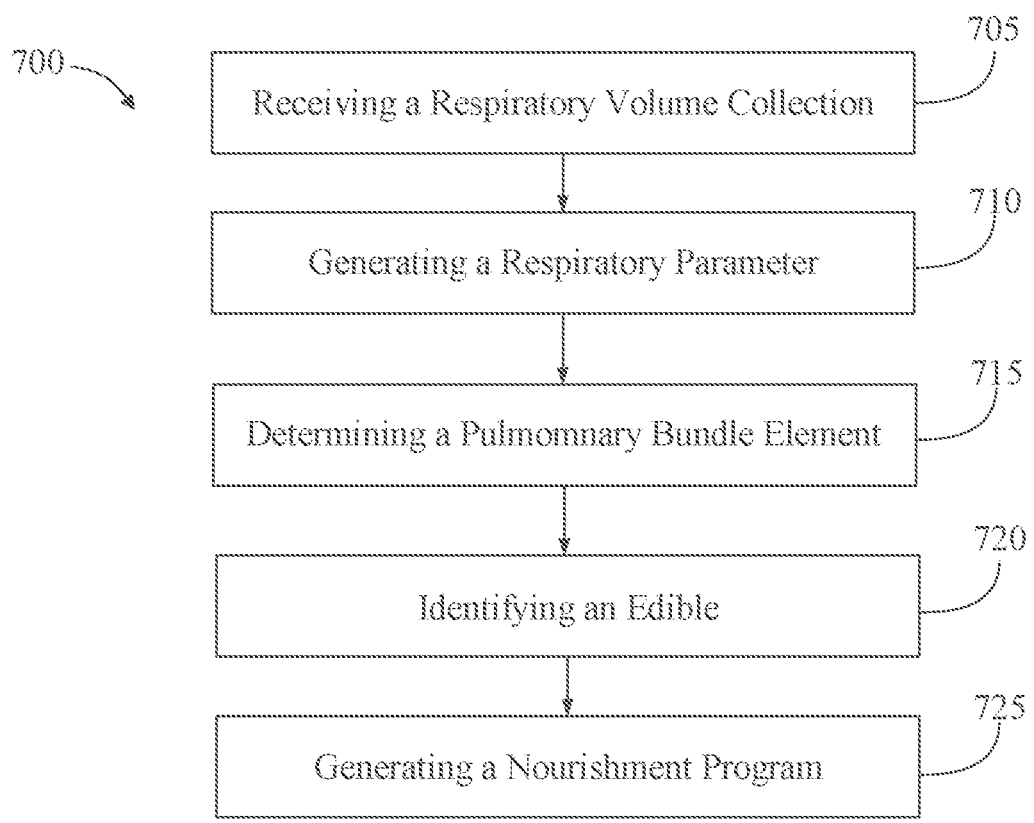
FIG. 7 is a process flow diagram illustrating an exemplary embodiment of a method of generating a pulmonary dysfunction nourishment program.

Now referring to FIG. 7, an exemplary embodiment of a method 700 for generating a pulmonary dysfunction nourishment program is illustrated. At step 705, a computing device 104 receives a respiratory collection 108. Computing device 104 includes any of the computing device 104 as described above, in reference to FIGS. 1-6. Respiratory volume collection 108 includes any of the respiratory volume collection 108 as described above, in reference to FIGS. 1-6. For instance, and without limitation, respiratory volume collection 108 may include one or more breath and/or blood samples provide by a user.

Still referring to FIG. 7, at step 710, computing device 104 generates at least a respiratory parameter 112 of a plurality of respiratory parameters as a function of respiratory volume collection 108. Respiratory parameter 112 includes any of the respiratory parameter 112 as described above, in reference to FIGS. 1-6. Computing device 104 generates respiratory parameter 112 using a respiratory algorithm 116. Respiratory algorithm 116 includes any of the respiratory algorithm 116 as described above, in reference to FIGS. 1-6.

Still referring to FIG. 7, at step 715, computing device 104 determines a pulmonary bundle element 120 as a function of respiratory parameter 112. Pulmonary bundle element 120 includes any of the pulmonary bundle element 120 as described above, in reference to FIGS. 1-6.

Still referring to FIG. 7, at step 720, computing device 104 identifies at least an edible 124 as a function of pulmonary bundle element 120. Edible 124 includes any of the edible 124 as described above, in reference to FIGS. 1-6. Edible 124 is identified by obtaining a nourishment composition 128 from an edible directory 132. Nourishment composition 128 includes any of the nourishment composition 128 as described above in reference to FIGS. 1-6. Edible directory 132 includes any of the edible directory 132 as described above, in reference to FIGS. 1-6. Edible 124 is identified by determining a nourishment deficiency 136 as a function of pulmonary bundle element 120. Nourishment deficiency 136 includes any of the nourishment deficiency 136 as described above, in reference to FIGS. 1-6. Edible 124 is identified using nourishment composition 128, nourishment deficiency 136, and an edible machine-learning model 140. Edible machine-learning model 140 includes any of the edible machine-learning model 140 as described above, in reference to FIGS. 1-6.

Still referring to FIG. 7, at step 725, computing device 104, outputs a nourishment program 144 of a plurality of nourishment programs as a function of edible 124. Nourishment program 144 includes any of the nourishment program 144 as described above, in reference to FIGS. 1-6.

Figure 8:
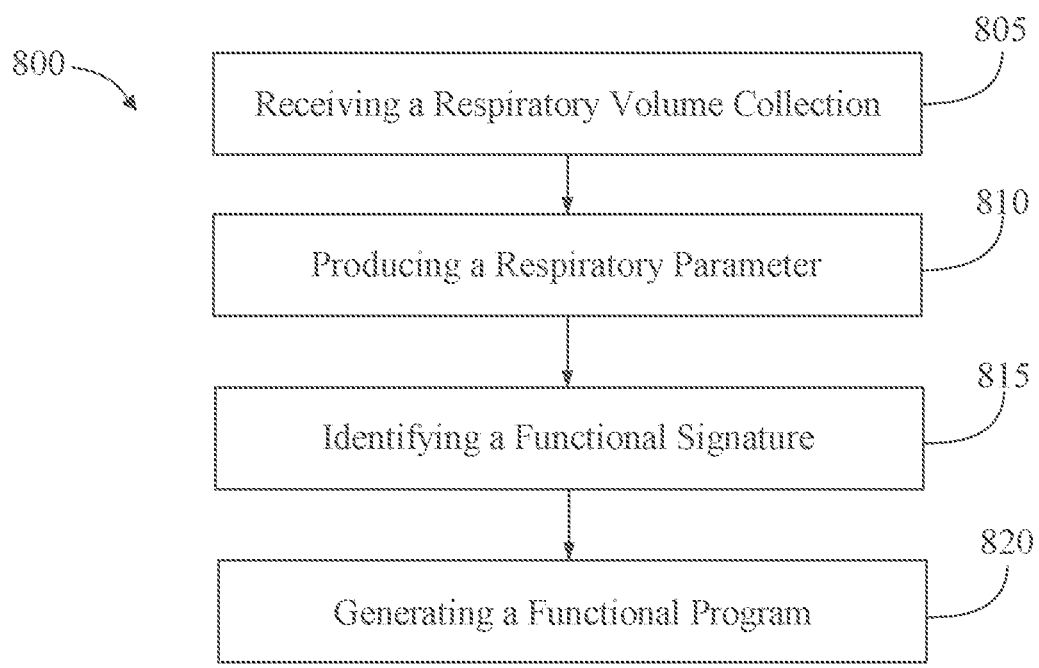
FIG. 8 is a process flow diagram illustrating an exemplary embodiment of a method of generating a pulmonary dysfunction functional program.

Now referring to FIG. 8, an exemplary embodiment of a method 800 for generating a pulmonary dysfunction functional program is illustrated. At step 805, a computing device 104 receives a respiratory collection 108. Computing device 104 includes any of the computing device 104 as described above, in reference to FIGS. 1-7. Respiratory volume collection 108 includes any of the respiratory volume collection 108 as described above, in reference to FIGS. 1-7. For instance, and without limitation, respiratory volume collection 108 may include one or more breath and/or blood samples provide by a user.

Still referring to FIG. 8, at step 810, computing device 104 produces at least a respiratory parameter 112 of a plurality of respiratory parameters as a function of respiratory volume collection 108. Respiratory parameter 112 includes any of the respiratory parameter 112 as described above, in reference to FIGS. 1-7. Computing device 104 generates respiratory parameter 112 using a respiratory algorithm 116. Respiratory algorithm 116 includes any of the respiratory algorithm 116 as described above, in reference to FIGS. 1-7.

Still referring to FIG. 8, at step 815, computing device 104 identifies functional signature 204. Functional signature 204 includes any of the functional signature 204 as described above, in reference to FIGS. 1-7. Computing device 104 identifies functional signature 204 as a function of receiving a conduct indicator 208. Conduct indicator 208 includes any of the conduct indicator 204 as described above, in reference to FIGS. 1-7. Computing device 104 identifies functional signature 204 as a function of conduct indicator 208 and pulmonary bundle element 120 using a functional machine-learning model 212. Functional machine-learning model 212 includes any of the functional machine-learning model 212 as described above, in reference to FIGS. 1-7.

Still referring to FIG. 8, at step, 820, computing device 104 generates a functional program 216 as a function of functional signature 204. Functional program 216 includes any of the functional program 216 as described above, in reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
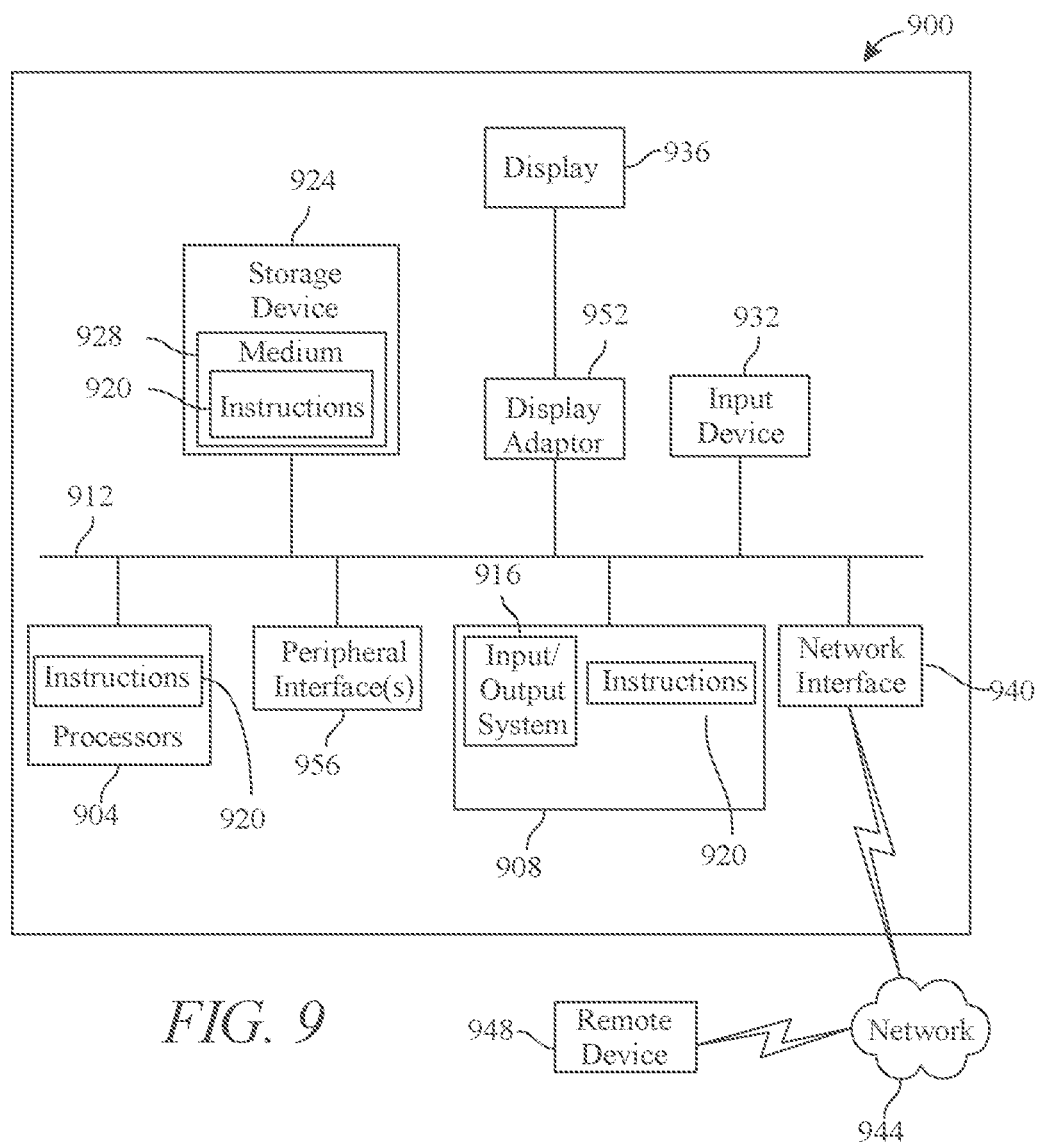
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a pulmonary dysfunction nourishment program, the system comprising:
   a computing device, the computing device configured to:
   receive at least a respiratory volume collection relating to a user, wherein the at least respiratory volume collection comprises at least a biomarker, wherein the at least biomarker comprises a bioremnant and a volatile organic compound (VOC);
   produce at least a respiratory parameter of a plurality of respiratory parameters as a function of the at least respiratory volume collection;
   receive a salubrious reference relating to the user, wherein the salubrious reference comprises a blood pressure reference;
   identify a functional signature as a function of the at least respiratory parameter and the salubrious reference, wherein the identifying further comprises:
   receiving a conduct indicator; and
   identifying the functional signature as a function of the conduct indicator, the at least respiratory parameter, the salubrious reference, and a functional machine-learning model; and
   generate the pulmonary dysfunction nourishment program as a function of the functional signature.

2. The system of claim 1, wherein identifying the functional signature further comprises determining a pulmonary dysfunction and identifying the functional signature as a function of the pulmonary dysfunction.

3. The system of claim 1, wherein the conduct indicator includes a dimensional element.

4. The system of claim 1, wherein receiving the conduct indicator further comprises obtaining an exposure element and receiving the conduct indicator as a function of the exposure element.

5. The system of claim 1, wherein identifying the functional signature further comprises:
   producing an indicator index as a function of the conduct indicator; and
   identifying the functional signature as a function of the indicator index.

6. The system of claim 1, wherein identifying the functional signature further comprises determining a root cause and identifying the functional signature as a function of the root cause.

7. The system of claim 1, wherein identifying the functional signature further comprises determining a habit as a function of the conduct indicator and identifying the functional signature as a function of the habit.

8. The system of claim 1, wherein generating the pulmonary dysfunction nourishment program further comprises:
  determining a holistic prospect; and
  generating the pulmonary dysfunction nourishment program as a function of the holistic prospect.

9. The system of claim 1, wherein the pulmonary dysfunction nourishment program includes a nourishment program.

10. The system of claim 1, wherein generating the pulmonary dysfunction nourishment program further comprises:
  obtaining a pulmonary functional goal; and
  generating the pulmonary dysfunction nourishment program as a function of the functional signature and the pulmonary functional goal using a goal machine-learning model.

11. A method for generating a pulmonary dysfunction nourishment program, the method comprising:
  receiving, by a computing device, at least a respiratory volume collection relating to a user, wherein the at least respiratory volume collection comprises at least a biomarker, wherein the at least biomarker comprises a bioremnant and a volatile organic compound (VOC);
  producing, by the computing device, at least a respiratory parameter of a plurality of respiratory parameters as a function of the at least respiratory volume collection;
  receiving, by the computing device, a salubrious reference relating to the user, wherein the salubrious reference comprises a blood pressure reference;
  identifying, by the computing device, a functional signature as a function of the at least respiratory parameter and the salubrious reference, wherein the identifying comprises:
  receiving a conduct indicator; and
  identifying the functional signature as a function of the conduct indicator, the at least respiratory parameter, the salubrious reference, and a functional machine-learning model; and
  generating, by the computing device, the pulmonary dysfunction nourishment program as a function of the functional signature.

12. The method of claim 11, wherein identifying the functional signature further comprises determining a pulmonary dysfunction and identifying the functional signature as a function of the pulmonary dysfunction.

13. The method of claim 11, wherein the conduct indicator includes a dimensional element.

14. The method of claim 11, wherein receiving the conduct indicator further comprises obtaining an exposure element and receiving the conduct indicator as a function of the exposure element.

15. The method of claim 11, wherein identifying the functional signature further comprises:
  producing an indicator index as a function of the conduct indicator; and
  identifying the functional signature as a function of the indicator index.

16. The method of claim 11, wherein identifying the functional signature further comprises determining a root cause and identifying the functional signature as a function of the root cause.

17. The method of claim 11, wherein identifying the functional signature further comprises determining a habit as a function of the conduct indicator and identifying the functional signature as a function of the habit.

18. The method of claim 11, wherein generating the pulmonary dysfunction nourishment program further comprises:
  determining a holistic prospect; and
  generating the pulmonary dysfunction nourishment program as a function of the holistic prospect.

19. The method of claim 11, wherein the pulmonary dysfunction nourishment program includes a nourishment program.

20. The method of claim 11, wherein generating the pulmonary dysfunction nourishment program further comprises:
  obtaining a pulmonary functional goal; and
  generating the pulmonary dysfunction nourishment program as a function of the functional signature.

* * * * *